United States Patent [19]

Scherzer et al.

[11] Patent Number: 5,208,368

[45] Date of Patent: May 4, 1993

[54] PREPARATION OF MIXTURES OF DIPHENYLMETHANE DIISOCYANATES AND POLYPHENYLPOLYMETHYLENE POLYISOCYANATES OF REDUCED IODINE COLOR NUMBER

[75] Inventors: Dietrich Scherzer, Ludwigshafen; Roland Minges, Gruenstadt; Bernd Bruchmann, Ludwigshafen; Wolfgang Heider, Limburgerhof; Willy van Pee, Kapellen; Peter Keller, Hirschberg, all of Fed. Rep. of Germany

[73] Assignee: BASF Aktiengesellschaft, Ludwigshafen, Fed. Rep. of Germany

[21] Appl. No.: 723,133

[22] Filed: Jun. 28, 1991

[30] Foreign Application Priority Data

Jul. 7, 1990 [DE] Fed. Rep. of Germany ....... 4021712

[51] Int. Cl.$^5$ .......................................... C07C 249/14
[52] U.S. Cl. .................................. 560/333; 560/347; 560/352
[58] Field of Search ......................... 560/333, 347, 352

[56] References Cited

U.S. PATENT DOCUMENTS 3,226,411 12/1965 Smith .................................. 560/333
3,394,164 7/1968 McClellan et al. ................ 560/333
3,449,256 6/1969 Farrissey et al. .................... 560/333
3,585,229 6/1971 Christian et al. .................... 560/333

*Primary Examiner*—José G. Dees
*Assistant Examiner*—Vera C. Clarke
*Attorney, Agent, or Firm*—Martin P. Connaughton

[57] ABSTRACT

Mixtures of diphenylmethane diisocyanates and polyphenylpolymethylene polyisocyanates (crude MDI) of reduced iodine color number are prepared by reacting the corresponding mixtures of diphenylmethanediamines and polyphenylpolymethylenepolyamines with phosgene in the presence of at least one inert organic solvent at elevated temperature, at least one monohydric or polyhydric polyoxyalkylene alcohol, preferably having a functionality of from 2 to 3, and advantageously having a hydroxyl number of from 20 to 1800, or mixtures thereof in an effective amount, expediently in an amount of from 0.1 to 10% by weight, based on the weight of the crude MDI, being introduced into the reaction mixture when the phosgenation is complete, the phosgene and the inert organic solvent then being removed, up to 5% by weight, based on the weight of crude MDI, of at least one phenol-based antioxidant and/or aryl phosphite being added, if desired to the reaction product, and the reaction mixture being heated.

12 Claims, No Drawings

PREPARATION OF MIXTURES OF DIPHENYLMETHANE DIISOCYANATES AND POLYPHENYLPOLYMETHYLENE POLYISOCYANATES OF REDUCED IODINE COLOR NUMBER

The present invention relates to a process for the preparation of mixtures of diphenylmethane diisocyanates and polyphenylpolymethylene polyisocyanates, known as crude MDI, of reduced iodine color number by reacting the corresponding mixtures of diphenylmethanediamines and polyphenylpolymethylene polyamines, known as crude MDA, with phosgene in the presence of at least one inert organic solvent, and incorporating monohydric or polyhydric polyoxyalkylene alcohols or mixtures thereof in an effective amount into the reaction mixture when the phosgenation is complete.

Crude MDI, one of the most important starting materials industrially for the preparation of polyisocyanate polyaddition products, for example foams containing urethane groups or containing urethane and isocyanurate groups, and of 4,4'-diphenylmethane diisocyanate, an important component in the preparation of polyurethane (PU) elastomers, fibers, sealants, adhesives, inter alia, is prepared, as is known, by phosgenating crude MDA, usually in the presence of an inert organic solvent. Crude MDA is itself obtained by condensing aniline and formaldehyde in the presence of an acidic catalyst, it being possible to control the percentage of diphenylmethanediamines and the homologous polyphenylpolymethylene polyamines and their isomers by means of the mixing ratios chosen from the starting materials, the reaction conditions and the various processes (Kunststoff-Handbuch, Volume 7, Polyurethane, 1st Edition 1966 and 2nd Edition 1983, Carl-Hanser-Verlag, Munich, Vienna). If the condensation of aniline and formaldehyde is carried out, for example, in the presence of a weakly acid catalyst, a crude MDA mixture having a relatively high level of 2,2'-and 2,4'-diaminodiphenylmethanes is obtained, while crude MDA mixtures having a high content of 4,4'-diaminodiphenylmethane and at the same time a low content of 2,4'-diaminodiphenylmethane can only be prepared in the presence of a relatively large amount of a highly acidic catalyst, preferably a strong mineral acid, e.g. hydrochloric acid.

The ratio between diaminodiphenylmethane isomers and the higher homologs in crude MDA is furthermore dependent on the aniline:formaldehyde ratio and the condensation temperature, relatively high aniline:formaldehyde ratios and low condensation temperatures giving high contents of diaminodiphenylmethane (CA-A-700,026).

These preparation processes, described in a large number of patent and other publications, have the disadvantage of the formation of crude MDA which is colored to a varying extent, the color varying from black via dark and pale brown shades to ocher. A further disadvantage is that this discoloration can only be reduced to an inadequate extent, if at all, even by subsequent phosgenation to prepare the corresponding crude MDI, and that the crude MDI formed cannot be purified by distillation. This undesired discoloration is also present in the secondary products, so that the cellular or noncellular polyisocyanate polyaddition products prepared from colored crude MDI are also colored. Although the inherent color of the polyisocyanate polyaddition products does not adversely affect the mechanical properties, the consumer desires essentially colorless products.

There has therefore been no lack of attempts to reduce the discoloration of crude MDI and to stabilize the prepared polyisocyanates by suitable process measures or by additives.

According to U.S. Pat. No. 2,885,420, organic polyisocyanates can be stabilized against discoloration by adding from 0.01 to 0.5% by weight, based on the weight of polyisocyanate, of an aromatic, cycloaliphatic or aliphatic ether or thioether.

According to DE-A-1 280 855 (GB 1,097,219), impurities which act as gelling catalysts in organic diisocyanate solutions are eliminated by adding from about 0.001 to 1% by weight of phosphoric acid, based on the weight of the diisocyanate.

GB-B-1,465,014 describes the addition of from 0.001 to 0.25% by weight, based on the weight of diisocyanate, of glycidol to improve the shelf life of distilled diphenylmethane diisocyanates.

EP-B-0 183 976 (U.S. Pat. No. 4,677,221) relates to a process for the preparation of (cyclo)aliphatic diisocyanates which are resistant to discoloration at elevated temperature in which technical grade diisocyanate containing aliphatically and/or cycloaliphatically bonded isocyanate groups is heated at from 100° to 220° C. for up to 5 hours in the presence of from 0.1 to 3% by weight of a compound which is soluble in the diisocyanate and contains at least 3% by weight of structural units of the formula —NH—CO—, and the diisocyanate treated in this way is subsequently purified by distillation. The process cannot be used to treat crude MDI since, as stated above, the latter cannot be distilled.

In U.S. Pat. No. 4,465,639, from 0.1 to 5% by weight of water, based on the weight of polyisocyanate in the reaction mixture, is introduced into crude MDI after the phosgenation is complete, but before all the phosgene has been removed. This measure lightens the color of crude MDI and of the PU foams produced therefrom. Furthermore, the proportion of relatively high-molecular-weight MDI homologs in the crude MDI is significantly reduced and their viscosity lowered. Although this method can reduce the iodine color number of crude MDI, it is also associated with considerable disadvantages. The presence of water considerably increases the corrosive effect of the reaction mixture, which contains chlorine, hydrogen chloride and phosgene, on the production plant and thereby increases the risk of leakage, with the release of toxic phosgene or a phosgene-containing reaction mixture. For safety reasons, moisture in any form is therefore expediently excluded completely during the phosgenation.

It is an object of the present invention to overcome the abovementioned disadvantages and to reduce the iodine color number of crude MDI to the level which can be achieved by adding water or even further, while, in particular, avoiding addition of water.

We have found that, surprisingly, this object is achieved by adding monohydric and/or polyhydric polyoxyalkylene alcohols to the phosgene-containing reaction mixture when the phosgenation is complete.

The present invention accordingly provides a process for the preparation of crude MDI of reduced iodine color number by reacting the corresponding crude MDA with phosgene in the presence of at least one inert organic solvent at elevated temperature, removing the excess phosgene and solvent when the phosgenation is complete, and heating the reaction product obtained, which comprises incorporating monohydric or polyhydric polyoxyalkylene alcohols, preferably polyhydric polyoxyalkylene alcohols having a functionality of from 2 to 8, or mixtures of monohydric and polyhydric polyoxyalkylene alcohols in an effective amount into the reaction mixture when the phosgenation is complete.

The addition according to the invention of the monohydric and/or polyhydric polyoxyalkylene alcohols can substantially reduce the iodine color number of crude MDI, for example to values of less than 60, preferably of from 35 to 20 or less.

The mixtures of diphenylmethane diisocyanates (MDI) and polyphenylpolymethylene polyisocyanates prepared by the process according to the invention furthermore advantageously contain from 30 to 90% by weight, preferably from 30 to 70% by weight, of MDI isomers, and $31\pm2\%$ by weight, preferably $31\pm1.0\%$ by weight, in each case based on the weight of crude MDI, of NCO and have a maximum viscosity of 2000 mPa.s, preferably from 40 to 350 mPa.s, measured at 23° C.

Crude MDI having isomer and homolog compositions of this type can, as stated above, be prepared by phosgenating crude MDA having an appropriate product composition by known processes in the presence of at least one inert organic solvent.

A suitable crude MDA is advantageously obtained by condensing aniline and formaldehyde in a molar ratio of from 6 to 1.6:1, preferably from 3 to 1.9:1, and an aniline:acidic catalyst molar ratio of from 1:0.98 to 0.01, preferably from 1:0.8 to 0.2.

The formaldehyde is preferably used in a form of an aqueous solution, for example as a commercially available 30 to 50% strength by weight solution.

Suitable acidic catalysts have proven to be proton donors, e.g. acidic ion exchanger resins or strong organic and preferably inorganic acids. For the purposes of the present invention, strong acids here are those having a $pK_a$ of less than 1.5 (for polybasic acids, this value applies to the first hydrogen dissociation). Examples which may be mentioned are hydrochloric acid, sulfuric acid, phosphoric acid, fluorosulfonic acid and oxalic acid. Hydrogen chloride can also be employed in gas form. Preference is given to aqueous hydrochloric acid in a concentration of from about 25 to 31% by weight.

Examples of suitable processes for the preparation of crude MDA are described in CA-A-700,026, DE-B-22 27 110 (U.S. Pat. No. 4,025,557), DE-B-22 38 920 (U.S. Pat. No. 3,996,283), DE-B-24 26 116 (GB-A-1,450,632), DE-A-12 42 623 (U.S. Pat. No. 3,478,099), GB-A-1,064,559 and DE-A-32 25 125.

The other starting component for the preparation of crude MDI is phosgene. The gaseous phosgene can be employed as such or diluted with a gas which is inert under the reaction conditions, such as nitrogen, carbon monoxide, inter alia. The crude MDA: phosgene molar ratio is expediently such that from 1 to 10 mol, preferably from 1.3 to 4 mol, of phosgene are present in the reaction mixture per $NH_2$ group.

Suitable inert organic solvents are compounds in which the crude MDA and the phosgene are at least partially soluble.

Highly suitable solvents are chlorinated, aromatic hydrocarbons, for example monochlorobenzene, dichlorobenzenes, e.g. o-dichlorobenzene and p-dichlorobenzene, trichlorobenzenes, the corresponding toluenes and xylenes, chloroethylbenzene, monochlorobiphenyl, α- and β-naphthyl chloride and dialkyl phthalates, such as diethyl isophthalate. The inert organic solvent is particularly preferably monochlorobenzene, dichlorobenzenes or mixtures of these chlorobenzenes. The solvents may be used individually or as mixtures. An expedient solvent has a lower boiling point than the MDI isomers so that the solvent can easily be separated from the crude MDI by distillation. The amount of solvent is expediently such that the reaction mixture contains from 2 to 40% by weight, preferably from 5 to 20% by weight, of isocyanate, based on the total weight of the reaction mixture.

The crude MDA can be used as such or dissolved in an organic solvent. However, preference is given to crude MDA solutions containing from 2 to 40% by weight, preferably from 5 to 20% by weight, of amine, based on the total weight of the amine solution.

To reduce the iodine color number, monohydric or preferably polyhydric polyoxyalkylene alcohols or mixtures thereof in an effective amount are introduced, according to the invention, into the phosgene-containing reaction mixture. Suitable polyoxyalkylene alcohols expediently have a hydroxyl number of from 20 to 1800, preferably from 100 to 1100, and in particular from 380 to 800, and the polyhydric polyoxyalkylene alcohols preferably have a functionality of from 2 to 8, in particular from 2 to 3. Particularly successful polyoxyalkylene alcohols are at least partially, but preferably completely, soluble, in the effective amounts necessary, in the inert organic solvent for the preparation of the crude MDI, preferably monochlorobenzene or a dichlorobenzene, or a mixture thereof.

The polyoxyalkylene alcohols can be prepared by known processes, for example by anionic polymerization using alkali metal hydroxides, e.g. sodium hydroxide or potassium hydroxide, or alkali metal alkoxides, such as sodium methoxide, sodium ethoxide, potassium ethoxide or potassium isopropoxide, as catalyst and with addition of at least one initiator molecule which contains at least one, preferably from 2 to 8, in particular 2 or 3, bonded reactive hydrogen atoms, or by cationic polymerization using Lewis acids, such as antimony pentachloride, boron fluoride etherate, inter alia, or bleaching earth as catalyst, from one or more alkylene oxides having from 2 to 4 carbon atoms in the alkylene radical.

Examples of suitable alkylene oxides are tetrahydrofuran, 1,3-propylene oxide, 1,2- and 2,3-butylene oxide, styrene oxide and preferably ethylene oxide and 1,2-propylene oxide. The alkylene oxides can be used individually, alternately one after the other or as mixtures. Examples of suitable initiator molecules are alkanols containing branched or preferably linear alkyl radicals having from 1 to 10, preferably from 1 to 4, carbon atoms, e.g. methanol, ethanol, n- and isopropanol, n- and sec-butanol, pentanol, hexanol and n- and isoctanols, polyhydric, preferably dihydric to octahydric, in particular dihydric and/or trihydric, alcohols or dialkylene glycols, e.g. ethanediol, 1,2- and 1,3-propanediol, diethylene glycol, dipropylene glycol, 1,4-butanediol, 1,5-pentanediol, 1,6-hexanediol, glycerol, trimethylolpropane, pentaerythritol, sorbitol and sucrose, and water.

Examples of suitable monohydric or polyhydric polyoxyalkylene alcohols are polyoxytetramethylene alcohol, polyoxytetramethylene-polyoxypropylene alcohol, polyoxytetramethylene-polyoxyethylene alcohol, polyoxypropylene alcohol, polyoxypropylene-polyoxyethylene alcohol and polyoxyethylene alcohol. However, particularly successful and therefore preferred, polyoxyalkylene alcohols are those having a functionality of from 2 to 3 and a hydroxyl number of from 380 to 800, expediently those prepared from ethylene oxide, 1,2-propylene oxide or 1,2-propylene oxide and ethylene oxide, it being possible for the polyoxypropylene-polyoxyethylene alcohols obtained to contain the ethylene oxide and 1,2-propylene oxide units bonded in a random distribution with ethylene oxide blocks. However, trifunctional polyoxypropylene-polyols having a hydroxyl number of from 380 to 600, which are expediently prepared using glycerol as the initiator molecule, are particularly suitable. The term polyoxyalkylene alcohols as used in connection with this invention also includes dialkylene glycols, preference being given to diethylene glycol, dipropylene glycol or mixtures thereof. The monohydric or polyhydric polyoxyalkylene alcohols may be used individually or in the form of mixtures. Naturally, mixtures of monohydric and polyhydric polyoxyalkylene alcohols are also suitable.

The amount of monohydric or polyhydric polyoxyalkylene alcohols necessary to reduce the iodine color number depends on the color and amount of impurities, which comprise one or more unknown substances, and the hydroxyl number of the polyoxyalkylene alcohols, and can be determined experimentally in a simple manner. Good results are usually achieved using from 0.1 to 10% by weight, based on the weight of the crude MDI in the reaction mixture, of at least one polyoxyalkylene alcohol, polyoxyalkylene alcohols having a hydroxyl number of less than 380 expediently being employed in an amount of from 2 to 10% by weight, in particular from 2 to 6% by weight, those having a hydroxyl number of from 380 to 800 expediently being employed in an amount of from 0.1 to 5% by weight, in particular from 0.2 to 3% by weight, and polyoxyalkylene alcohols having a hydroxyl number of greater than 800 expediently being employed in an amount of from 0.1 to 3% by weight, in particular from 0.1 to 1.5% by weight, in each case based on the weight of the solvent-free crude MDI.

The polyoxyalkylene alcohols may be employed in a pure or commercially available quality, but the water content of the commercially available products should be as low as possible, expediently less than 0.1% by weight.

After the excess phosgene and the insert solvent has been removed, at least one phenol-based antioxidant, at least one aryl phosphite or a mixture of these stabilizers may, if desired, be added to the crude MDI containing monohydric and/or polyhydric polyoxyalkylene alcohols and/or reaction products obtainable from these monohydric and/or polyhydric polyoxyalkylene alcohols and crude MDI. If used, these stabilizers, which can additionally reduce the iodine color number in combination with the polyoxyalkylene alcohols used according to the invention, are expediently used in an amount of from 0 to a maximum of 5% by weight, preferably from 0.01 to 3% by weight, in particular from 0.1 to 1.0% by weight, based on the weight of the crude MDI.

Examples of suitable phenol-based antioxidants are styrene-modified phenols, i.e. phenols which contain a 1-phenylethyl group bonded in the 2- or 4-position or in the 2- and 4- and/or 6-position, bis[2-hydroxy-5-methyl-3-tert-butylphenyl]methane, 2,2-bis[4-hydroxyphenyl]-propane, 4,4'-dihydroxybiphenyl, 3,3'-dialkyl- or 3,3',5,5'-tertraalkyl-4,4'-dihydroxybiphenyl, bis[4-hydroxy-2-methyl-5-tert-butylphenyl] sulfide, hydroquinone, 4-methoxy-, 4-tert-butoxy- or 4-benzyloxyphenol, mixtures of 4-methoxy-2-and -3-tert-butylphenol, 2,5-dihydroxyl-1-tert-butylbenzene, 2,5-dihydroxy-1,4-di-tert-butylbenzene, 4-methoxy-2,6-di-tert-butylphenol and preferably 2,6-di-tert-butyl-p-cresol.

Suitable aryl phosphites are tri(alkylphenyl) phosphites having from 1 to 10 carbon atoms in the alkyl radical, e.g. tri(methylphenyl) phosphite, tri(ethylphenyl) phosphite, tri(n-butylphenyl phosphite tri(sec-butylphenyl) phosphite, tri(tert-butylphenyl) phosphite, tri(2-ethylhexylphenyl) phosphite tri(octyphenyl) phosphite, tri(2-ethyloctylphenyl) phosphite, tri(decylphenyl) phosphite, preferably tri(nonylphenyl) phosphite, in particular triphenyl phosphite.

To prepare the crude MDI of reduced iodine color number, by the process according to the invention, the corresponding crude MDA is expediently phosgenated at from 90° to 220° C., preferably from 120° to 180° C., at superatmospheric pressure, for example at from 1 to 10 bar, preferably from 1 to 3 bar, or in particular at atmospheric pressure. The temperature used in the process according to the invention is above the decomposition point of the carbamoyl chlorides formed as intermediates due to reaction of crude MDA with phosgene. There are only technical and possibly safety limits on an increase in pressure, but increases in yield are no longer associated with relatively large increases in pressure.

When the phosgenation is complete, the monohydric and/or preferably polyhydric polyoxyalkylene alcohol, in particular glycerol-initiated polyoxypropylene-polyol, is introduced at from 20° to 150° C., preferably from 70° to 120° C., in particular from 80° to 110° C., into the reaction mixture, which comprises at least one inert organic solvent, dissolved crude MDI, excess phosgene, hydrogen chloride and phosgenation by-products and which usually has a phosgene content of less than 20% by weight, preferably 0.01 to 3% by weight and in particular 0.1 to 2% by weight, based on the total weight. After a residence time of from 0.1 to 45 minutes, preferably from 2 to 25 minutes, at from 20° to 150° C., preferably from 70° to 120° C., the excess phosgene is removed essentially completely, preferably by distillation, at atmospheric pressure and subsequently at from 30° to 180° C., preferably from 50° to 150° C., and the inert organic solvent or mixtures thereof under reduced pressure, for example at from 0.01 50 mbar.

At least one phenol-based antioxidant and/or at least one aryl phosphite in an effective amount can now, if it appears expedient, be added to the crude MDI containing monohydric and/or preferably polyhydric polyoxyalkylene alcohols and/or products of the reaction of these polyoxyalkylene alcohols with crude MDI. The crude MDI treated in this way is then dechlorinated by heating to from 100° to 250° C., preferably from 140 ° to 200° C., and treated at this temperature at a pressure of from 0.01 to 100 mbar, preferably from 0.1 to 20 mbar, for at least 5 minutes, in particular for from 5 to 45 minutes. After cooling to 60° C., the crude MDI is fed to an interim storage tank, where it is allowed to cool further.

The crude MDI prepared by the process according to the invention has a significantly reduced iodine color number, usually a maximum of 60, and is used to produce compact or foamed polyisocyanate polyaddition products, preferably flexible, semihard or hard foams containing urethane groups or containing urethane and isocyanurate groups and having a significant paler color.

EXAMPLES 1 to 16

The monohydric or polyhydric polyoxyalkylene alcohols were added at from 100° to 105° C. to a reaction mixture which comprised, based on 100 parts by weight, 82 parts by weight of monochlorobenzene as solvent, 8 parts by weight of excess phosgene and 10 parts by weight of crude MDI, which itself contained:
- 50% by weight of 4,4'-MDI
- 4% by weight of 2,4'-MDI
- 0.04% by weight of 2,2'-MDI and
- 45.96% by weight of homologs containing more than two isocyanate groups, based on the weight of crude MDI, and unidentified secondary components.

The reaction mixture was then warmed to 140° C. over the course of approximately 20 minutes, and the excess phosgene was distilled off under atmospheric pressure over the course of 20 minutes using a rotary evaporator.

The reaction mixture was subsequently allowed to cool to from 100° to 120° C. for about 10 minutes, and essentially all the monochlorobenzene was distilled off in this temperature range under reduced pressure (from 50 to 10 mbar) over the course of about 15 minutes.

The crude MDI containing monohydric and/or polyhydric polyoxyalkylene alcohols employed and their amounts are given in the table below, along with the iodine color numbers (ICN) measured for the crude MDI obtained.

The iodine color number was determined in accordance with DIN 6162 by diluting the crude MDI with monochlorobenzene in the volume ratio 1:5.

In the table:
PO: denotes 1,2-propylene oxide units
EO: denotes ethylene oxide units
(number): denotes the amount of PO or EO units in % by weight, based on the total weight of PO and EO units

TABLE 1

| | | Monohydric or polyhydric polyoxyalkylene alcohols added when phosgenation complete | | Crude MDI obtained Properties | | | |
|---|---|---|---|---|---|---|---|
| | | Amount | | | | | |
| Example | Starting materials | [% by weight, based on Crude MDI] | Type | OH number | ICN (1:5) | NCO content [% by weight] | Viscosity [mPa · s] |
| | Crude MDI | — | — | — | 90 | 32.1 | 50 |
| 1 | " | 5 | Glycerol-PO(87)-EO(13) | 35 | 50 | 30.7 | 66 |
| 2 | " | 10 | Glycerol-PO(87)-EO(13) | 35 | 40 | 28.5 | 88 |
| 3 | " | 4 | Glycerol-PO(26)-EO(74) | 42 | 50 | 30.7 | 65 |
| 4 | " | 10 | Glycerol-PO(26)-EO(74) | 42 | 25 | 29.0 | 108 |
| 5 | " | 2 | Methanol-PO | 108 | 60 | 31.2 | 53 |
| 6 | " | 4 | Polyoxytetramethylene glycol | 176 | 50 | 31.1 | 47 |
| 7 | " | 10 | Polyoxytetramethylene glycol | 176 | 20 | 28.9 | 72 |
| 8 | " | 1 | Glycerol-PO | 400 | 35 | 31.7 | 53 |
| 9 | " | 4 | Glycerol-PO | 400 | 27 | 30.0 | 90 |
| 10 | " | 10 | Glycerol-PO | 400 | 20 | 27.2 | 326 |
| 11 | " | 0.5 | Glycerol-PO | 560 | 30 | 32.2 | 44 |
| 12 | " | 1 | Glycerol-PO | 560 | 32 | 31.9 | 48 |
| 13 | " | 1.5 | Glycerol-PO | 560 | 20 | 31.5 | 73 |
| 14 | " | 1 | Glycerol-EO | 749 | 28 | 31.7 | 50 |
| 15 | " | 1 | Glycerol-PO | 1120 | 20 | 32.0 | 48 |
| 16 | " | 1 | Glycerol-EO | 1240 | 23 | 31.9 | 55 |

EXAMPLES 17 TO 22

The procedure according to Examples 1 to 16 was followed, except that use was made of a reaction mixture which comprised, based on 100 parts by weight, 88.6 parts by weight of monochlorobenzene as solvent, 0.6 parts by weight of excess phosgene, and 10.8 parts by weight of crude MDI, which itself contained:
- 50% by weight of 4,4'-MDI,
- 4% by weight of 2,4'-MDI,
- 0.04% by weight of 2,2'-MDI, and
- 45.96% by weight of homologs containing more than two isocyanate groups, based on the weight of crude MDI, and unidentified secondary components.

The dialkylene glycols or polyoxyalkylene triols and their amounts as well as the iodine color numbers measured for the crude MDI obtained are given in Table 2 below.

TABLE 2

| | | Monohydric or polyhydric polyoxyalkylene alcohols added when phosgenation complete | | Crude MDI obtained | |
|---|---|---|---|---|---|
| | | Amount | | | |
| Example | Starting materials | [% by weight based on crude MDI] | Type | OH Number | Iodine color Number (1:5) |
| | Crude MDI | — | — | — | 80 |
| 17 | | 0.2 | Diethyleneglycol | 1059 | 35 |
| 18 | | 0.2 | Diethyleneglycol | 836 | 35 |
| 19 | | 0.2 | Glycerol-PO | 1120 | 50 |
| 20 | | 1.0 | Glycerol-PO | 1120 | 18 |
| 21 | | 1.0 | Glycerol-EO | 749 | 25 |
| 22 | | 1.0 | Glycerol-EO | 1240 | 19 |

We claim:

1. A process for the preparation of mixtures of diphenylmethane diisocyanates and polyphenylpolymethylene polyisocyanates of reduced iodine color number, by reacting the corresponding mixtures of diphenylmethanediamines and polyphenylpolymethylene polyamines with phosgene in the presence of at least one inert organic solvent at elevated temperature, removing the excess phosgene and solvent when the phosgenation is complete, and heating the reaction product, the improvement which comprises incorporating monohydric or polyhydric polyoxyalkylene alcohols or mixtures thereof in an effective amount into the reaction mixture when the phosgenation is complete.

2. A process as claimed in claim 1, wherein the monohydric or polyhydric polyoxyalkylene alcohols have a hydroxyl number of from 20 to 1800.

3. A process as claimed in claim 1, wherein the monohydric or polyhydric polyoxyalkylene alcohols or mixtures thereof are incorporated into the reaction mixture in an amount of from 0.1 to 10% by weight, based on the weight of the mixture of diphenylmethane diisocyanates and polyphenylpolymethylene polyisocyanates.

4. A process as claimed in claim 1, wherein the polyhydric polyoxyalkylene alcohols have a functionality of from 2 to 3 and a hydroxyl number of from 100 to 1100.

5. A process as claimed in claim 4, wherein the polyhydric polyoxyalkylene alcohol used is a trifunctional polyoxypropylene-polyol having a hydroxyl number of from 380 to 600.

6. A process as claimed in claim 1, wherein the polyhydric polyoxyalkylene alcohols are diethylene glycol, dipropylene glycol or mixtures thereof.

7. A process as claimed in claim 1, wherein the reaction mixture has a phosgene content of from 0.01 to 3% by weight, based on the total weight.

8. A process as claimed in claim 1, wherein the inert organic solvent used for the preparation of the mixtures of diphenylmethane diisocyanates and polyphenylpolymethylene polyisocyanates is monochlorobenzene, and the monohydric or polyhydric polyoxyalkylene alcohols or mixtures thereof employed are at least partially soluble in this solvent.

9. A process as claimed in claim 1, wherein the monohydric or polyhydric polyoxyalkylene alcohols are selected from the group consisting of polyoxyethylene alcohol, polyoxypropylene alcohol, polyoxypropylene-polyoxyethylene alcohol, or mixtures thereof.

10. A process as claimed in claim 1, wherein the resulting mixtures of diphenylmethane diisocyanates and polyphenylpolymethylene polyisocyanates contain from 30 to 90% by weight of diphenylmethane diisocyanate isomers, and 31±2% by weight of NCO, in each case based on the total weight, and have a maximum viscosity of 2000 mPa.s at 23° C. and a maximum iodine color number of 60.

11. A process as claimed in claim 1, further having at least one phenol-based antioxidant in a maximum amount of 5% by weight and/or at least one aryl phosphite in a maximum amount of 5% by weight, in each case based on the weight of the mixture of diphenylmethane diisocyanates and polyphenylpolymethylene polyisocyanates, incorporated into the monohydric or polyhydric polyoxyalkylene alcohol-containing mixture of diphenylmethane diisocyanates and polyphenylpolymethylene polyisocyanates after the excess phosgene and the inert organic solvent have been removed and before the reaction product has been heated.

12. A process as claimed in claim 1, wherein from 0.01 to 5% by weight of a trifunctional polyoxypropylene-polyol, based on the weight of the mixture of diphenylmethane diisocyanates and polyphenylpolymethylene polyisocyanates in the reaction mixture, is incorporated into the reaction mixture when the phosgenation is complete, the excess phosgene and the inert organic solvent are then removed by distillation, from 0 to 5% by weight of di-tert-butyl-p-cresol and/or triphenyl phosphite, based on the weight of the mixture of diphenylmethane diisocyanates and polyphenylpolymethylene polyisocyanates, is added to the reaction mixture, and the reaction product is then heated.

* * * * *